United States Patent [19]

Taylor

[11] 4,187,848

[45] Feb. 12, 1980

[54] ADAPTER ASSEMBLY

[75] Inventor: Glenn N. Taylor, Cary, Ill.

[73] Assignee: The Kendall Company, Boston, Mass.

[21] Appl. No.: 959,961

[22] Filed: Nov. 13, 1978

Related U.S. Application Data

[63] Continuation of Ser. No. 816,553, Jul. 18, 1977, abandoned.

[51] Int. Cl.² .............................................. A61M 3/00
[52] U.S. Cl. .................................. 128/247; 128/349 R
[58] Field of Search ............ 128/218 R, 214 R, 214.2, 128/215, 216, 272.3, 247, 349 R, 221, 220

[56] References Cited

U.S. PATENT DOCUMENTS

| | | | |
|---|---|---|---|
| 3,270,767 | 9/1966 | Hirsch | 128/247 X |
| 3,918,450 | 11/1975 | Patel | 128/247 |
| 3,977,403 | 8/1976 | Patel | 128/247 X |

FOREIGN PATENT DOCUMENTS

| | | | |
|---|---|---|---|
| 496910 | 12/1938 | United Kingdom | 128/218 R |
| 837661 | 6/1960 | United Kingdom | 128/218 R |
| 1430092 | 3/1976 | United Kingdom | 128/218 R |

*Primary Examiner*—John D. Yasko
*Attorney, Agent, or Firm*—Powell L. Sprunger

[57] ABSTRACT

An adapter assembly comprising, a syringe having a tip, a catheter, and a connector having a body member, a compressible plug, and a compression member. The body member has a bore to receive the plug, and an opening communicating with the bore. The plug has a channel to receive the catheter through the body member opening into the plug channel. The compression member has a nipple receivable in a proximal end of the body member bore, and a proximal port to receive the syringe tip. The compression member may be releasably attached to the body member in such a manner that the nipple bears against the plug and secures the catheter in the plug channel, while the syringe may be attached to the compression member with the syringe tip received in the compression member port.

7 Claims, 8 Drawing Figures

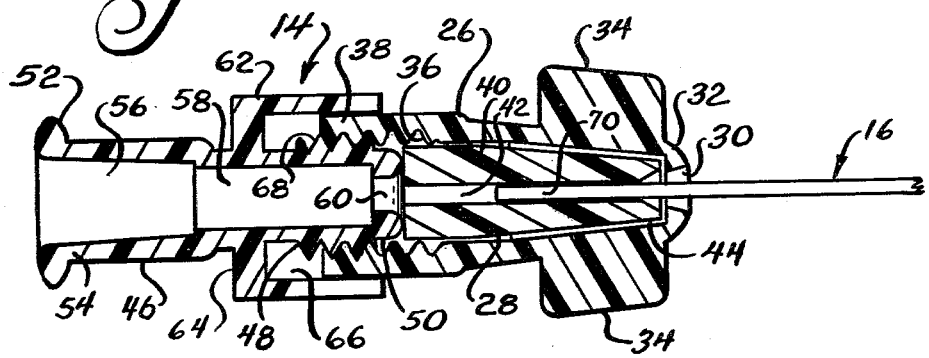
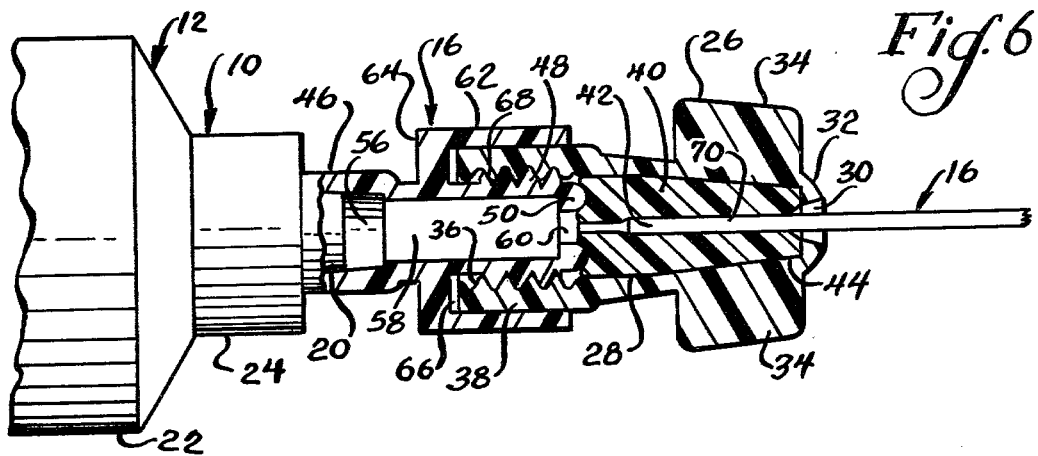
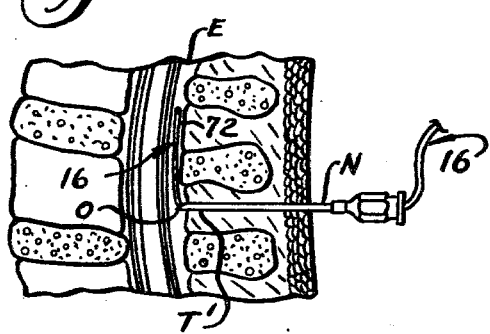
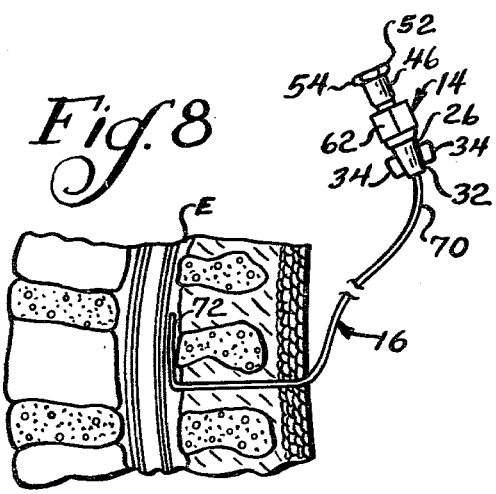

4,187,848

ADAPTER ASSEMBLY

This is a continuation of application Ser. No. 816,553, filed July 18, 1977, now abandoned.

BACKGROUND OF THE INVENTION

The present invention relates to adapter assemblies.

During certain medical procedures, for example a continuous epidural or caudal spinal anesthesia procedure, it is necessary to connect a syringe to an end of a catheter. In a continuous epidural anesthesia procedure, a needle is positioned in a patient's body with an opening at one end of the needle positioned in the epidural space of the patient and with the other end of the needle extending outside the patient's body. A catheter of relatively small diameter is threaded through the needle and the needle opening until a distal end of the catheter is located in the epidural space, while a proximal end of the catheter extends outside the patient's body. The needle is removed from the patient's body and from the catheter to prevent obstruction if the operation takes place with the patient lying on his back and to prevent the needle from cutting the catheter during the operation. After removal of the needle, an anesthetic solution is injected through the catheter into the epidural space by a syringe which is connected to the proximal end of the catheter.

Accordingly, a connector or adapter must be provided for connecting the syringe to the proximal end of the catheter. The adapter should be positionable on the catheter after removal of the needle from the catheter, since the adapter would otherwise prevent removal of the needle from the catheter. It is also desirable that the adapter should permit easy placement on the catheter to expedite the procedure.

After the syringe has been connected to the adapter, the anesthetic solution is injected through the catheter into the epidural space. A relatively large amount of the solution is initially required for epidural anesthesia, with additional amounts of the solution being periodically injected during surgery. it is preferred that the syringe be removed from the adapter between injections, since if the syringe remains connected to the adapter and if the syringe inadvertently falls from the bed or other structure on which it is placed, the weight of the connected syringe may pull the catheter from the patient's body, necessitating repositioning of the catheter into the epidural space during surgery if further anesthesia is required.

SUMMARY OF THE INVENTION

A principal feature of the present invention is the provision of a connector of simplified construction which facilitates attachment to the tip of a syringe and a catheter.

The connector comprises, a body member having an elongated bore and an opening adjacent a distal end portion of the body member communicating with the bore. The connector has an elongated plug of elastic material received in the bore in a relatively uncompressed condition of the plug. The plug has a channel extending through the plug with the channel aligned with the body member opening and with the internal dimensions of the channel being slightly larger than the outer dimensions of the catheter. The connector has a compression member having a nipple adjacent a distal end of the compression member and receivable in a proximal end portion of the body member. The compression member has a port adjacent a proximal end portion of the compression member to receive the syringe tip, and a passageway communicating between the port and the distal end of the nipple, with a distal portion of the passageway being aligned with the plug channel when the nipple is received in the body member bore. The connector has means for releasably attaching the compression member to the body member with the nipple received in the bore, and for controlling the distance the nipple projects into the bore.

A feature of the present invention is that the catheter may be readily inserted through the body member opening and into the plug channel while the plug is in its relatively uncompressed condition.

Another feature of the invention is that the compression member may be attached to the body member such that communication is established between the syringe port and the plug channel.

Still another feature of the invention is that the distance which the compression member nipple extends into the body member bore may be controlled such that the nipple bears upon the plug and releasably locks the catheter in the plug channel.

Yet another feature of the invention is that the syringe may be releasably attached to a proximal end portion of the compression member with the syringe tip received in the compression member port.

Thus, a feature of the present invention is that the catheter may be readily secured in the connector, and the syringe may be attached to the connector in order to pump liquid through the connector into the catheter.

A further feature of the invention is the provision of a gripping element on the compression member which overlies a proximal end portion of the body member in order to facilitate removal of the syringe from the connector without releasing the catheter from the compressed plug.

Further features will become more fully apparent in the following description of the embodiments of this invention and from the appended claims.

DESCRIPTION OF THE DRAWINGS

In the drawings:

FIG. 5 is a sectional view of the connector with the catheter received in a compressible plug of the connector;

FIG. 6 is a fragmentary elevational view, taken partly in section, showing the catheter locked in the connector and the syringe attached to the connector; and FIGS. 7 and 8 are diagrammatic views of a patient's body illustrating steps during placement of a catheter in the epidural space of the patient.

DESCRIPTION OF THE PREFERRED EMBODIMENTS

Figure 1:
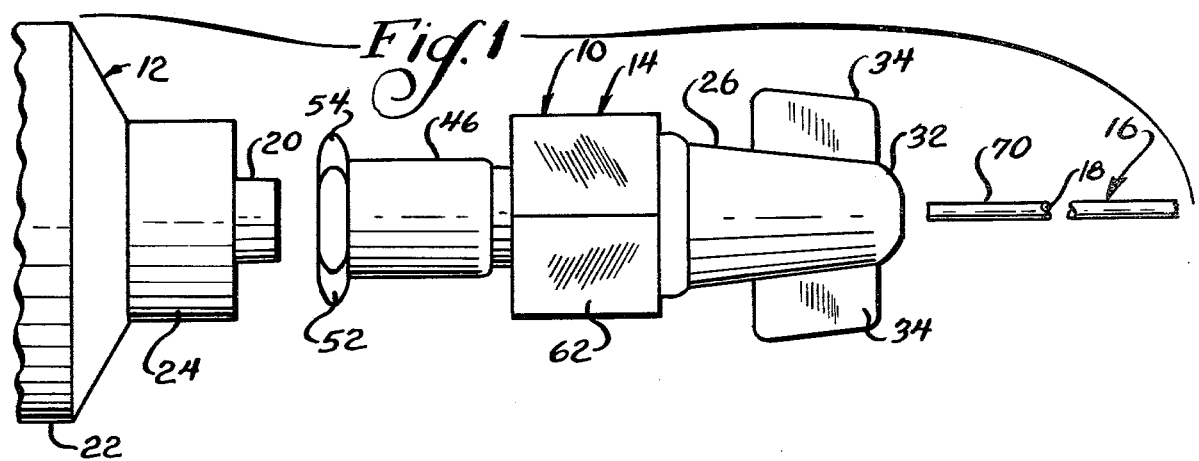
FIG. 1 is a fragmentary elevational view of an adapter assembly of the present invention having a connector, a catheter, and a syringe.
Figure 2:
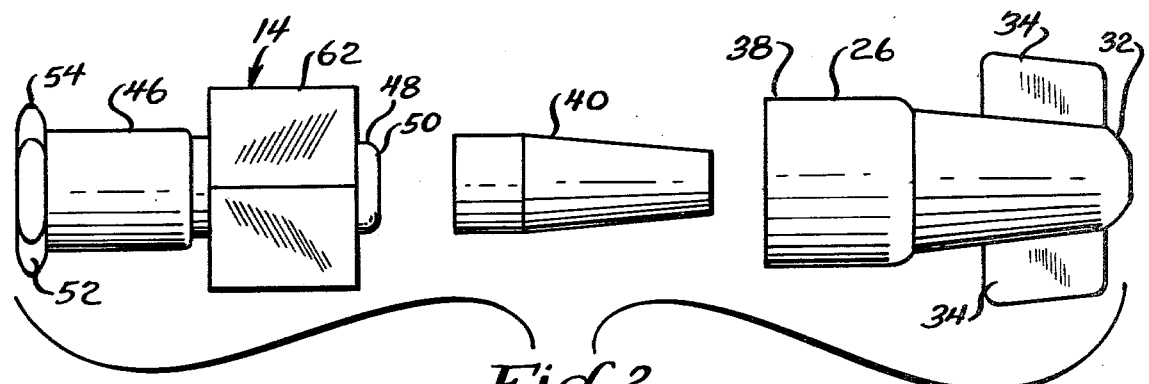
FIG. 2 is an exploded elevational view of the connector of FIG. 1.
Figure 3:
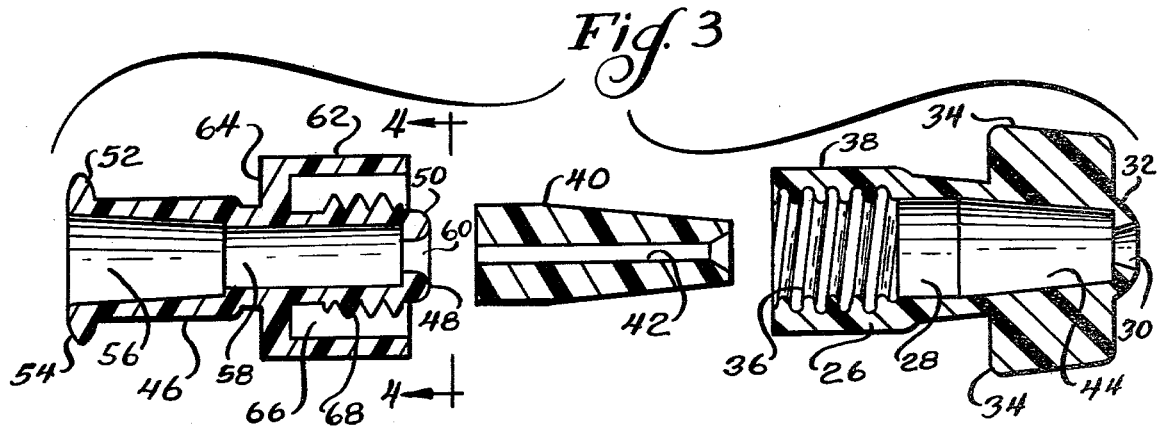
FIG. 3 is an exploded sectional view of the connector of FIG. 2.
Figure 4:
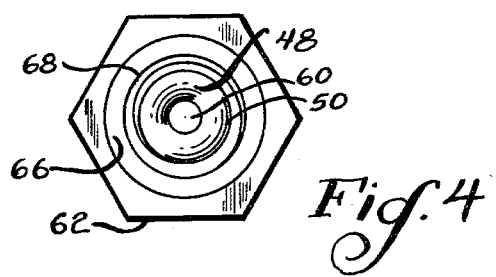
FIG. 4 is an end view of a compression member taken substantially as indicated along the line 4—4 of FIG. 3.

Referring now to FIGS. 1-4, there is shown an adapter assembly generally designated 10 comprising a syringe 12, a connector 14, and an elongated relatively thin catheter 16 having a lumen 18. The syringe 12 has a tip 20 communicating with a chamber in a syringe barrel 22, and a luer fitment 24 for releasable attachment of the syringe to the connector 14.

The connector 14 has a body member 26 having an elongated bore 28, an opening 30 at a distal end 32 of the body member 26, a pair of opposed outwardly directed wings 34 adjacent the distal end 32 of the body member 26, and internal threads 36 at the proximal end 38 of the body member 26. The connector 14 also has an elongated plug 40 of elastic material having a channel 42 extending longitudinally through the plug 40, with the inner dimensions of the plug channel 42 being slightly larger than the outer dimensions of the catheter 16 when the plug 40 is in a relatively uncompressed condition. As shown, both the plug 40 and the body member bore 28 have associated distal conical sections and proximate cylindrical sections, such that the plug 40 may be received in a distal end portion 44 of the body member bore 28 in a relatively uncompressed condition of the plug 40, with the plug channel 42 being aligned with the body member opening 30, and with the distal end of the plug channel 42 and the body member opening 30 defining a distal taper to facilitate placement of the catheter in the plug channel 42.

The connector 14 also has a compression member 46 having a nipple 48 at a distal end 50 of the compression member 46. The compression member 46 also has an outwardly directed luer flange 52 at a proximal end 54 of the compression member 46, and a tapered port 56 to receive the tapered syringe tip 20, such that the syringe 12 may be releasably locked to the connector 14 through cooperation of the luer fitment 24 and the luer flange 52 with the syringe tip 20 being received in the connector port 56. The compression member 46 has a passageway 58 communicating between the port 56 and an aperture 60 at the distal end 50 of the compression member nipple 48 which defines a distal ring 61 surrounding the aperture 60. The compression member 46 has a distally directed gripping element 62 which extends circumferentially around the nipple 48, with the gripping element 62 being connected to a mid-portion of the compression member 46 by a flange 64, such that the gripping element 62 and compression nipple 48 define an annular cavity 66 for a purpose which will be described below. As shown, the nipple 48 has outer threads 68 which cooperate with the threads 36 of the body member 26.

The body member 26 and compression member 46 may be made of any suitable material, such as plastic. The plug 40 may be made of any suitable elastic material, such as rubber or Kraton, a trademark of Shell Oil Company.

The connector 14 is shown in an assembled configuration in FIG. 5. Thus, the plug 40 is received in the distal portion 44 of the body member bore 28 in a relatively uncompressed condition of the plug, and the compression member 46 may be releasably attached to the body member 26 through cooperation of the body member threads 36 and the compression member threads 68, with the proximal end 38 of the body member 26 being received in the cavity 66 of the compression member 46 intermediate the gripping element 62 and the nipple 48, and with the distal portion of passageway 58 being aligned with the plug channel 42. In the configuration of FIG. 5, the distal end of the nipple 48 slightly contacts the proximal end of the plug 40, and a proximal end 70 of the catheter 16 may be readily inserted into the plug channel 42, since the plug 40 remains in a relatively uncompressed condition at this time. As previously noted, the distal taper of the plug channel 42 and the body member opening 30 facilitates guidance and placement of the catheter 16 into the plug channel 42.

With reference to FIG. 6, the compression member 46 may be further rotated relative the body member 26, such that the cooperating threads cause distal movement of the compression member nipple 48 in the body member bore 28. Thus, the distal ring 61 of the compression member nipple 48 bears upon the compressible plug 40 in order to reduce the effective size of the plug channel 42, cuasing the compressed plug to grip the catheter in the plug channel 42 and lock the catheter in the connector 14. In this configuration, the gripping element 62 overlies the proximal end 38 of the body member 26, with the proximal end 38 of the body member 26 being received in the compression member cavity 66. At this time, the syringe 12 may be attached to the proximal end of the compression member 46 in a manner as previously described.

Thus, the catheter may be readily inserted into the plug channel 42 of the connector 14, and the catheter may be locked in place by relative rotation of the compression member 46 and body member 26. Next, the syringe 12 may be attached to the connector 14 in order to establish communication between the syringe tip and the catheter lumen. In this manner, the connector 14 is attached to the catheter 16 in a simplified manner to permit ejection of fluid into the catheter lumen when it is desired to do so by attaching the syringe to the connector and by pumping the syringe, However, after an initial quantity of liquid has been ejected from the syringe into the catheter lumen, it is preferred to remove the syringe from the connector. The physician may simultaneously grasp the gripping element 62 and an exposed portion of the body member 26 with the fingers of one hand, and the physician may then remove the syringe with the other hand. Thus, the gripping element 62 permits removal of the syringe 12 from the connector 14 while preventing rotation of the compression member 46 relative the body member 26 which otherwise might inadvertently release the catheter from the previously compressed plug 40.

The use of the connector for a continuous epidural spinal anesthesia procedure is described in connection with FIGS. 7 and 8 as follows, although it will be understood that the assembly may be utilized for other suitable purposes, such as a continuous caudal spinal anesthesia procedure. With reference to FIG. 7, the tip T' of a Hustead needle N is inserted through the skin S' of the patient until an opening O in the needle tip T' is located in the epidural space E. Next, a distal end 72 of the catheter 16 is threaded through the needle N and opening O to position the distal end 72 of the catheter 16 in the epidural space E, as shown. The desired length of the catheter distal end 16 located in the epidural space E may be determined by suitable gradations spaced along the outer surface of the catheter. In this configuration, the catheter 16 extends outside the patient's body. The needle N is then removed from the patient's body and from the catheter 16 to prevent the needle from inadvertently cutting the catheter during surgery.

With reference to FIG. 8, after the needle has been removed from the catheter, the proximal end 70 of the catheter 16 is inserted into the connector 14 and locked in place, in a manner as previously described. Next, the syringe is attached to the connector 14 to pump a quantity of anesthetic solution from the syringe through the connector and catheter into the spidural space E. When the desired amount of anesthetic solution has been injected into the epidural space, the syringe is removed from the connector 14.

Accordingly, the adapter assembly permits easy placement of the connector 14 on the proximal end 10 of the catheter 16. The syringe may be readily attached to the connector 14, such that communication is established between the syringe and the catheter 16. After the desired amount of solution has been injected into the epidural space, the syringe may be removed from the connector.

The foregoing detailed description is given for clearness of understanding only, and no unnecessary limitations should be understood therefrom, as modifications will be obvious to those skilled in the art.

I claim:

1. An adapter assembly, comprising:
a syringe having a tip;
a catheter; and
a connector comprising, a body member having an elongated bore and an opening adjacent a distal end portion of the body member communicating with said bore, an elongated plug of elastic material received in said bore in a relatively uncompressed condition of the plug, said plug having a channel extending through the plug with a distal portion of the channel being aligned with the body member opening and with the internal dimensions of at least a distal portion of the channel being slightly larger than the outer dimensions of said catheter to receive the catheter through said body member opening, a compression member having a nipple adjacent a distal end of the compression member and receivable in a proximal end portion of the body member, said compression member having a port adjacent a proximal end portion of the compression member to receive the syringe tip, and a passageway communicating between the port and the distal end of said nipple, with a distal portion of said passageway being aligned with the plug channel when the nipple is received in the body member bore, and means for releasably attaching the compression member to the body member with said nipple received in said bore, and for controlling the distance said nipple projects into said bore such that the nipple compresses said plug in the bore and releasably secures the catheter in said plug channel, said compression member including a distal gripping element defining a space intermediate the gripping element and said nipple to receive the proximal end portion of the body member when the nipple is received in the body member bore.

2. The assembly of claim 1 wherein the attaching and controlling means comprises cooperating threads on the inner surface of the body member proximal end portion and on the outer surface of said compression member nipple.

3. The assembly of claim 1 wherein said compression member includes a distal gripping element defining a space intermediate the gripping element and said nipple to receive the proximal end portion of the body member when the nipple is received in the body member bore.

4. The assembly of claim 1 wherein said gripping element extends circumferentially around said nipple and defines an annular cavity to receive the proximal end portion of said body member, and in which the compression member includes a flange connecting the gripping element to the compression member intermediate proximal and distal ends of the compression element.

5. The assembly of claim 1 wherein the body member includes a pair of opposed outwardly directed wings to facilitate manipulation of the body member.

6. The assembly of claim 1 including means for releasably attaching the syringe to said compression member with the syringe tip received in said port.

7. The assembly of claim 1 wherein said body member opening and a distal end portion of the plug channel define a distal taper to facilitate placement of the catheter in the plug channel.

* * * * *